United States Patent
Daly et al.

(10) Patent No.: US 10,874,603 B2
(45) Date of Patent: *Dec. 29, 2020

(54) SUNSCREEN COMPOSITIONS CONTAINING A UV-ABSORBING POLYGLYCEROL AND A NON-UV-ABSORBING POLYGLYCEROL

(71) Applicant: JOHNSON & JOHNSON CONSUMER INC., Skillman, NJ (US)

(72) Inventors: Susan Daly, Basking Ridge, NJ (US); Prithwiraj Maitra, Hillsborough, NJ (US); Barry Setiawan, Skillman, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 632 days.

This patent is subject to a terminal disclaimer.

(21) Appl. No.: 14/674,536

(22) Filed: Mar. 31, 2015

(65) Prior Publication Data
US 2015/0320671 A1   Nov. 12, 2015

Related U.S. Application Data

(60) Provisional application No. 61/991,732, filed on May 12, 2014.

(51) Int. Cl.
| | | |
|---|---|---|
| *A61K 8/86* | (2006.01) | |
| *A61Q 17/04* | (2006.01) | |
| *A61K 8/34* | (2006.01) | |
| *A61Q 19/00* | (2006.01) | |

(52) U.S. Cl.
CPC .............. *A61K 8/86* (2013.01); *A61Q 17/04* (2013.01); *A61K 2800/30* (2013.01); *A61K 2800/57* (2013.01)

(58) Field of Classification Search
CPC .. A61K 8/86; A61K 2800/57; A61K 2800/30; A61K 8/345; A61Q 17/04; A61Q 19/00
See application file for complete search history.

(56) References Cited

U.S. PATENT DOCUMENTS

| | | | |
|---|---|---|---|
| 4,107,290 A | 8/1978 | Jacquet et al. | |
| 4,322,522 A | 3/1982 | Johnson et al. | |
| 4,399,297 A | 8/1983 | Thoemel et al. | |
| 4,528,311 A | 7/1985 | Beard et al. | |
| 4,839,160 A | 6/1989 | Forestier et al. | |
| 4,897,259 A | 1/1990 | Murray et al. | |
| 5,039,782 A | 8/1991 | Langer et al. | |
| 5,041,281 A | 8/1991 | Strobridge | |
| 5,138,089 A | 8/1992 | Sabatelli | |
| 5,157,091 A | 10/1992 | Masataka et al. | |
| 5,166,234 A | 11/1992 | Kawaguchi et al. | |
| 5,250,652 A | 10/1993 | Langer et al. | |
| 5,399,371 A | 3/1995 | Harris | |
| 5,459,222 A | 10/1995 | Rodgers et al. | |
| 5,487,885 A | 1/1996 | Sovak et al. | |
| 5,585,090 A | 12/1996 | Yoshioka et al. | |
| 5,674,475 A * | 10/1997 | Dahms ..................... A61K 8/06 424/59 |
| 5,741,924 A | 4/1998 | Sovak et al. | |
| 5,843,410 A | 12/1998 | Kim et al. | |
| 5,869,030 A | 2/1999 | Dumler et al. | |
| 5,869,099 A | 2/1999 | Keller et al. | |
| 6,001,337 A | 12/1999 | Keller et al. | |
| 6,048,516 A | 4/2000 | Bringhen et al. | |
| 6,123,928 A | 9/2000 | Sovak et al. | |
| 6,143,850 A | 11/2000 | Keller et al. | |
| 6,183,728 B1 | 2/2001 | Forestier et al. | |
| 6,294,156 B1 | 9/2001 | Lentini et al. | |
| 6,391,287 B1 | 5/2002 | Baldo et al. | |
| 6,413,393 B1 | 7/2002 | Van Antwerp et al. | |
| 6,471,949 B2 | 10/2002 | Candau et al. | |
| 6,540,986 B2 | 4/2003 | Lukenbach et al. | |
| 6,620,407 B1 | 9/2003 | Gers-Barlag et al. | |
| 6,620,904 B2 | 9/2003 | Lemke | |
| 6,767,547 B2 | 7/2004 | Gers-Barlag et al. | |
| 6,800,274 B2 | 10/2004 | Bonda et al. | |
| 6,814,959 B1 | 11/2004 | Muller et al. | |
| 6,867,250 B1 | 3/2005 | Gupta et al. | |
| 6,869,597 B2 | 3/2005 | Arnaud | |
| 6,881,415 B1 | 4/2005 | Gers-Barlag et al. | |
| 6,899,866 B2 | 5/2005 | Bonda | |
| 6,905,674 B2 | 6/2005 | L'Alloret | |
| 6,951,911 B2 | 10/2005 | Tagawa et al. | |

(Continued)

FOREIGN PATENT DOCUMENTS

| | | |
|---|---|---|
| DE | A 2 024051 | 5/1986 |
| EP | 407932 A | 1/1991 |

(Continued)

OTHER PUBLICATIONS

U.S. Appl. No. 13/926,248, filed Jun. 25, 2013, US20140004063A1, Daly.
U.S. Appl. No. 13/926,282, filed Jun. 25, 2013, US20140004064A1, Daly.
U.S. Appl. No. 61/665,464, filed Jun. 28, 2012, Daly.
U.S. Appl. No. 13/710,531, filed Dec. 11, 2012, US20140004057A1, Daly et al.
U.S. Appl. No. 14/565,909, filed Dec. 10, 2014, US20150093341A1, Daly et al.
U.S. Appl. No. 13/535,890, filed Jun. 28, 2012, US20140004054A1, Daly et al.
U.S. Appl. No. 13/710,546, filed Dec. 11, 2012, US20140004058A1, Daly et al.

(Continued)

*Primary Examiner* — Abigail Vanhorn
(74) *Attorney, Agent, or Firm* — Sharon E. Hayner

(57) ABSTRACT

A sunscreen composition including a polymer composition that contains a UV-absorbing polyglycerol having a UV-absorbing chromophore chemically bound thereto, and a cosmetically-acceptable topical carrier that contains at least one percent by weight of the sunscreen composition of a non-UV-absorbing polyglycerol, based on total weight of the sunscreen composition.

19 Claims, 1 Drawing Sheet

(56) References Cited

U.S. PATENT DOCUMENTS

| | | |
|---|---|---|
| 6,962,692 B2 | 11/2005 | Bonda et al. |
| 6,989,151 B2 | 1/2006 | Gers-Barlag et al. |
| 7,008,618 B1 | 3/2006 | Hessefort et al. |
| 7,087,692 B2 | 8/2006 | Koshti et al. |
| 7,097,828 B2 | 8/2006 | Meyer et al. |
| 7,153,494 B2 | 12/2006 | Chodorowski et al. |
| 7,186,415 B1 | 3/2007 | Gers-Barlag et al. |
| 7,264,795 B2 | 9/2007 | Pflücker et al. |
| 7,427,640 B1 | 9/2008 | Katayama et al. |
| 7,465,438 B2 | 12/2008 | Schunicht et al. |
| 7,534,420 B2 | 5/2009 | Bonda et al. |
| 7,749,524 B2 | 7/2010 | Lu et al. |
| 7,850,954 B2 | 12/2010 | Leblanc et al. |
| 7,914,775 B2 | 3/2011 | Cottard et al. |
| 7,988,953 B2 | 8/2011 | Poschalko et al. |
| 7,993,680 B2 | 8/2011 | Clemente et al. |
| 8,003,132 B2 | 8/2011 | Clemente et al. |
| 8,025,868 B2 | 9/2011 | Clemente et al. |
| 8,211,850 B2 | 7/2012 | Andjelic et al. |
| 8,394,755 B2 | 3/2013 | Andjelic et al. |
| 2001/0038829 A1 | 4/2001 | Hasebe et al. |
| 2002/0131941 A1 | 9/2002 | Habeck et al. |
| 2002/0155073 A1 | 10/2002 | Fankhauser et al. |
| 2003/0165553 A1 | 9/2003 | Gers-Barlag et al. |
| 2004/0019220 A1 | 1/2004 | Fischer et al. |
| 2004/0022836 A1 | 2/2004 | Degen et al. |
| 2004/0057914 A1 | 3/2004 | Bonda et al. |
| 2004/0096406 A1 | 5/2004 | De Poilly |
| 2004/0126339 A1 | 7/2004 | Roszell |
| 2004/0197359 A1 | 10/2004 | Yamada et al. |
| 2004/0223925 A1 | 11/2004 | L'Alloret |
| 2004/0228814 A1 | 11/2004 | Candau et al. |
| 2005/0031660 A1 | 2/2005 | Deckner |
| 2005/0036961 A1 | 2/2005 | Hansenne et al. |
| 2005/0048010 A1 | 3/2005 | Kliss et al. |
| 2005/0065251 A1 | 3/2005 | Candau et al. |
| 2005/0180933 A1 | 8/2005 | Wei et al. |
| 2006/0204457 A1 | 9/2006 | Toda et al. |
| 2007/0098653 A1 | 5/2007 | Tamasawa et al. |
| 2007/0134174 A1 | 6/2007 | Irwin et al. |
| 2008/0081025 A1 | 4/2008 | Poschalko et al. |
| 2008/0089852 A1 | 4/2008 | Hotz et al. |
| 2008/0247975 A1 | 10/2008 | Dueva-Koganov et al. |
| 2008/0311234 A1 | 12/2008 | Yoneda et al. |
| 2009/0016971 A1 | 1/2009 | Gaudry et al. |
| 2009/0041688 A1 | 2/2009 | Dueva-Koganov et al. |
| 2009/0068130 A1 | 3/2009 | Spaulding et al. |
| 2009/0185988 A1 | 7/2009 | Maleski et al. |
| 2009/0214460 A9 | 8/2009 | Luukas |
| 2009/0232859 A1 | 9/2009 | Sakuta et al. |
| 2009/0258230 A1 | 10/2009 | Schlossman et al. |
| 2009/0297462 A1 | 12/2009 | Hessefort et al. |
| 2009/0324523 A1 | 12/2009 | Clemente et al. |
| 2009/0324524 A1 | 12/2009 | Clemente et al. |
| 2010/0003202 A1 | 1/2010 | Matsumoto et al. |
| 2010/0129303 A1 | 5/2010 | Dueva-Koganov et al. |
| 2010/0189661 A1 | 7/2010 | Musa et al. |
| 2010/0226867 A1 | 9/2010 | Dueva-Koganov et al. |
| 2010/0239508 A1 | 9/2010 | Mori et al. |
| 2010/0284948 A1 | 11/2010 | Ohrmann et al. |
| 2011/0014139 A1 | 1/2011 | Viala et al. |
| 2011/0027202 A1 | 2/2011 | Candau et al. |
| 2011/0082105 A1 | 4/2011 | Fevola et al. |
| 2011/0104078 A1 | 5/2011 | Burgo et al. |
| 2011/0117034 A1* | 5/2011 | Satonaka ............... A61K 8/39 424/59 |
| 2011/0195036 A1 | 8/2011 | Clemente et al. |
| 2012/0058974 A1 | 3/2012 | Misske et al. |
| 2012/0087882 A1 | 4/2012 | Fevola et al. |
| 2012/0093753 A1 | 4/2012 | Fevola et al. |
| 2012/0282201 A1* | 11/2012 | Schlifke-Poschalko ................... A61K 8/86 424/60 |
| 2012/0294813 A1 | 11/2012 | Frey et al. |
| 2013/0004553 A1 | 1/2013 | Takakura et al. |
| 2013/0115179 A1 | 5/2013 | Janssen et al. |
| 2014/0004063 A1 | 1/2014 | Daly |
| 2014/0004064 A1 | 1/2014 | Daly |

FOREIGN PATENT DOCUMENTS

| | | |
|---|---|---|
| EP | 413648 A | 2/1991 |
| EP | 523955 A | 1/1993 |
| EP | 601080 B | 7/1995 |
| EP | 681830 A | 11/1995 |
| EP | 1051963 A | 11/2000 |
| EP | 1291370 A | 3/2003 |
| EP | 1089986 B | 3/2005 |
| EP | 2015727 B | 1/2010 |
| EP | 2198930 A | 6/2010 |
| EP | 2679616 A | 1/2014 |
| EP | 2876126 A | 5/2015 |
| EP | 2886101 A | 6/2015 |
| FR | A 2 252 840 | 6/1975 |
| JP | S6099186 A | 6/1985 |
| JP | 2006-265389 A | 10/2006 |
| JP | 2009-167168 A | 7/2009 |
| RU | 2162686 C2 | 2/2001 |
| RU | 2009124703 | 1/2011 |
| WO | WO 1992/19214 | 11/1992 |
| WO | WO 1992/019592 A | 11/1992 |
| WO | WO 1993/022366 A | 11/1993 |
| WO | WO 1993/022413 A | 11/1993 |
| WO | WO 1996/003369 A | 2/1996 |
| WO | WO 2000/066675 A | 11/2000 |
| WO | WO 2001/008647 A | 2/2001 |
| WO | WO 2002/024668 A | 3/2002 |
| WO | WO 2002/036534 A | 5/2002 |
| WO | WO 2004/009047 A | 1/2004 |
| WO | WO 2005/092282 A | 10/2005 |
| WO | WO 2007/066309 A | 6/2007 |
| WO | WO 2007/081209 A | 7/2007 |
| WO | WO 2007092407 A2 | 8/2007 |
| WO | WO 2008/056678 A | 5/2008 |
| WO | WO 2010/060776 A | 6/2010 |
| WO | WO 2010/115009 A | 10/2010 |
| WO | WO 2010136360 A2 | 12/2010 |
| WO | WO 2011003774 A2 | 1/2011 |
| WO | WO 2011/048570 A | 4/2011 |
| WO | WO 2011/070050 A | 6/2011 |
| WO | WO 2011/070053 A | 6/2011 |
| WO | WO 2011/070073 A | 6/2011 |
| WO | WO 2011/070075 A | 6/2011 |
| WO | WO 2011/070077 A | 6/2011 |
| WO | WO 2011098315 A1 | 8/2011 |
| WO | WO 2012129722 | 10/2012 |
| WO | WO 2013076691 | 5/2013 |
| WO | WO 2014/004474 A | 1/2014 |
| WO | WO 2014/004477 A | 1/2014 |
| WO | WO 2015122770 A1 | 8/2015 |
| WO | WO 2017/218390 A | 12/2017 |

OTHER PUBLICATIONS

U.S. Appl. No. 14/565,968, filed Dec. 10, 2014, US20150086495A1, Daly et al.

U.S. Appl. No. 13/535,899, filed Jun. 28, 2012, US20140004055A1, Daly et al.

U.S. Appl. No. 13/710,555, filed Dec. 11, 2012, US20140004059A1, Daly et al.

U.S. Appl. No. 14/566,063, filed Dec. 10, 2014, US20150098916A1, Daly et al.

U.S. Appl. No. 13/535,909, filed Jun. 28, 2012, US20140004056A1, Daly et al.

U.S. Appl. No. 14/132,290, filed Dec. 18, 2013, Daly et al.

U.S. Appl. No. 61/991,732, filed May 12, 2014, Daly et al.

U.S. Appl. No. 13/799,193, filed Mar. 13, 2013, US20140004060A1, Levins et al.

U.S. Appl. No. 61/665,430, filed Jun. 28, 2012, Levins et al.

U.S. Appl. No. 13/799,222, filed Mar. 13, 2013, US20140004061A1, Levins et al.

(56) References Cited

OTHER PUBLICATIONS

U.S. Appl. No. 61/665,439, filed Jun. 28, 2012, Levins et al.
"Crodacol™ C95 Product Details" from the Croda website, 2013 http://www.croda.com/home.aspx?view=dtl&d=content&s=157&r=401&p=2578&prodlD-1779.
Erberich et al., "Polyglycidols with Two Orthogonal Protective Groups: Preparation, Selective Deprotection, and Functionalization", *Macromolecules* (2007), vol. 40, pp. 3070-3079.
Evans et al., "The Colloidal Domain: where physics, chemistry, biology, and technology meet," Wiley, 1999, p. 409-416; http://www.bre.orst.edu/Courses/Colloid%20Transport/documents/DLVOPrimer.pdf.
Fitton et al., Synthesis (1987), pp. 1140-1142.
Hanson et al., "Sunscreen Enhancement of UV-induced Reactive Oxygen Species in the Skin", *Free Radical Biology & Medicine* (2006) vol. 41, pp. 1205-1212.
Haouet et al., "Preparation Et Proprietes Des Poly®-Glycidols", *European Polymer Journal* (1983), vol. 19(12), pp. 1089-1098. (English Abstract).
Kuhn et al., "Monitoring the Kinetics of Ion-Dependent Protein Folding by Time-Resolved NMR Spectroscopy at Atomic Resolution", *Journal of the American Chemical Society* (2000), vol. 122, pp. 6169-6174.
Lee et al., "Poly(allyl Glycidyl Ether)—A Versatile and Functional Polyether Platform", *Journal of Polymer Science Part A: Polymer Chemistry* (2011), vol. 49, pp. 4498-4504.
Li et al., "Synthesis of polyethylene glycol (PEG) derivatives and PEGylated-peptide biopolymer conjugates", *Biomacromolecules*, American Chemical Society, US, vol. 4, No. 4, May 17, 2003, pp. 1055-1067 (ISSN: 1525-7797, DOI: 10.1021/BM034069L) (XP002328259).
Moore et al., "Room Temperature Polyesterification", *Macromolecules* (1990), vol. 23, Issue 1, pp. 65-70.
Obermeier et al., "Poly(ethylene glycol-co-allyl glycidyl ether)s: A PEG-Based Modular Synthetic Platform for Multiple Bioconjugation", Bioconjugate Chemistry (2011), vol. 22, pp. 436-444.
Rokicki et al., "Hyperbranched aliphatic polyethers obtained from environmentally benign monomer: glycerol carbonate", *Green Chemistry* (2005), vol. 7, pp. 529-539.
Stiriba et al., "Hyperbranched molecular nanocapsules: Comparison of the hyperbranched architecture with the perfect linear analogue", Journal of the american Chemical Society (2002) vol. 124, pp. 9698-9699.
Sunder et al., "Controlled Synthesis of Hyperbranched Polyglycerols by Ring-Opening Multibranching Polymerization", *Macromolecules* (1999), vol. 32, pp. 4240-4246.
Taton et al., "Synthesis of chiral and racemic functional polymers from glycidol and thioglycidol", *Macromolecular Chemistry and Physics* (1994), vol. 195, pp. 139-148.
Tchao, "Trans-Epithelial Permeability of Fluorescein In Vitro as an Assay to Determine Eye Irritants", *Alternative Methods in Toxicology 6, Progress in In Vitro Toxicology* (ed. A.M. Goldberg) (1988), pp. 271-283.
Tokar et al., "Cationic Polymerization of Glycidol: Coexistence of the Activated Monomer and Active Chain End Mechanism", *Macromolecules* (1994), vol. 27, pp. 320-322.
U.S. Appl. No. 15/648,503, filed Jul. 13, 2017, Daly.
U.S. Appl. No. 15/648,507, filed Jul. 13, 2017, Daly.
U.S. Appl. No. 62/404,246, filed Oct. 5, 2016, Daly et al.
U.S. Appl. No. 15/686,382, filed Aug. 25, 2017, Daly et al.
Graham, A.B. et al., Inhibition of the Mitochondrial Oxidation of octanoate by Salicylic Acid and related Compounds, J. Pharm. Pharmacol. 26, pp. 531-534 (1973).
Jakobson, G., Diglycerin und hoehere Oligomere des Glycerins als Synthesebausteine, Fette, Seifen Anstrichmittel, 1986, vol. 88, pp. 101-106.
Lochhead, R.Y. et al., Cosmetics and Toiletries, vol. 108, pp. 95-135 (1993).
Todd, C. et al., Volatile Silicone Fluids for Cosmetic Formulations, Cosmetics and Toiletries, vol. 91, pp. 29-32 (1976).
Tronnier, H. et al., J. Soc. Cosm. Chem. 24, pp. 281-290 (1973).
Wenk, H.H. et al., Polyglycerol—A Versatile Building Block for Sustainable Cosmetic Raw Materials, SOFW-Journal, 2009, vol. 135, Issue 8, pp. 25-30.
Anonymous: "Personal Care SUNSPHERES ™ Hollow Sphere Technology an APF Booster for More Aesthetically Pleasing Formulations Features, Benefits and Applications", Feb. 28, 2006 (Feb. 28, 2006), pp. 1-14, XP055321502, Retrieved from the Internet: URL:http://www.dow.com/assests/attachments/business/pcare/sunspheres/sunspheres_powder/tds/sunspheres_powder.pdf.
U.S. Appl. No. 62/350,863, filed Jun. 16, 2016, Daly et al.
U.S. Appl. No. 62/362,251, filed Jul. 14, 2016, Daly et al.
U.S. Appl. No. 62/378,736, filed Aug. 24, 2016, Daly et al.
Im et al., "Analysis of Polymeric UV Absorber Tinuvin 213 using LDI-TOFMS: solvent effect in sample preparation", Bull. Korean Chem. Soc., Jun. 20, 2011, 32(6):2093-2096 (XP002776302).
European search report dated Sep. 21, 2015, for corresponding EP application 15167207.8.

\* cited by examiner

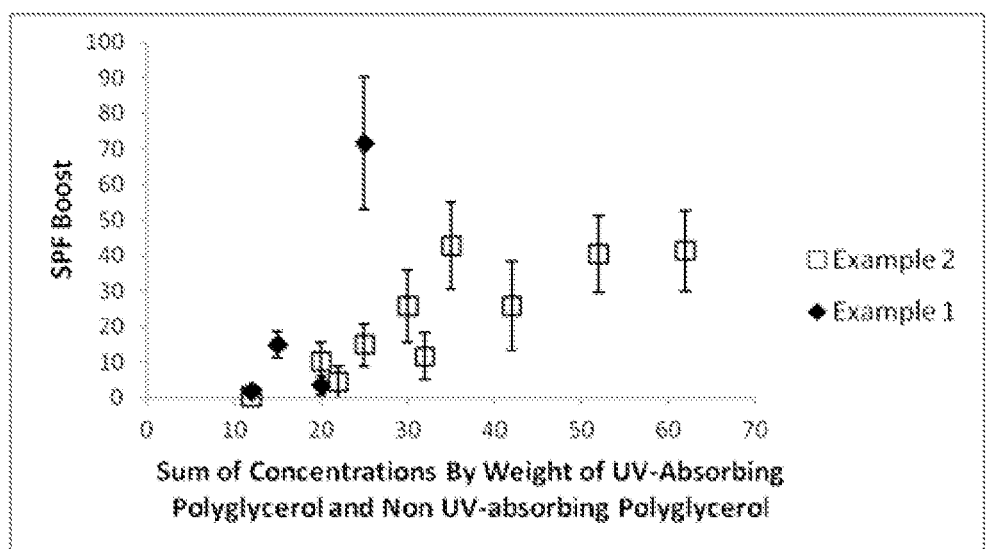

SUNSCREEN COMPOSITIONS CONTAINING A UV-ABSORBING POLYGLYCEROL AND A NON-UV-ABSORBING POLYGLYCEROL

This application claims the benefit of U.S. provisional application 61/991,732 filed on May 12, 2014, the complete disclosure of which is hereby incorporated herein by reference for all purposes.

FIELD OF THE INVENTION

The present invention relates to sunscreen compositions comprising a polymer composition comprising a UV-absorbing polyglycerol and a non-UV-absorbing polyglycerol.

BACKGROUND OF THE INVENTION

The prolonged exposure to ultraviolet radiation (UV), such as from the sun, can lead to the formation of light dermatoses and erythemas, as well as increase the risk of skin cancers, such as melanoma, and accelerate skin aging, such as loss of skin elasticity and wrinkling.

Numerous sunscreen compositions are commercially available with varying ability to shield the body from ultraviolet light. However, numerous challenges still exist to provide sunscreen compositions that provide strong UV radiation protection.

One approach to providing UV protection is to employ sunscreen compositions having UV-absorbing polymers. The inventors of the instant invention, however, have recognized that compositions having UV-absorbing polymers may require high concentrations of UV-absorbing polymer in order to provide high levels UV-protection (e.g., SPF). Accordingly, the inventors have identified that a need exists to have sunscreen compositions that include UV-absorbing polymers, yet still provide sufficient SPF, among other potential benefits such as good aesthetics.

SUMMARY OF THE INVENTION

The present invention relates to sunscreen compositions comprising a polymer composition which comprises an ultraviolet radiation absorbing, i.e. a UV-absorbing, polyglycerol having a UV-absorbing chromophore chemically bound thereto; and a cosmetically-acceptable topical carrier, wherein the cosmetically-acceptable topical carrier comprises a non-UV-absorbing polyglycerol, and wherein the non-UV-absorbing polyglycerol is present in the sunscreen composition at a concentration by weight of at least one percent, based on total weight of the sunscreen composition.

DESCRIPTION OF THE DRAWINGS

FIG. 1 represents the difference in SPF versus the amounts of UV-absorbing polyglycerols and non-UV-absorbing polyglycerols.

DETAILED DESCRIPTION OF THE INVENTION

Unless defined otherwise, all technical and scientific terms used herein have the same meaning as commonly understood by one of ordinary skill in the art to which the invention belongs. As used herein, unless otherwise indicated, all hydrocarbon groups (e.g., alkyl, alkenyl) groups may be straight or branched chain groups. As one skilled in the art will readily recognize, since the UV-absorbing polyglycerol and non-UV-absorbing polyglycerol described herein are polymers, the chemical features thereof, e.g., molecular weight, degree of polymerization, carbon chain lengths, and the like, are characterized as having a statistical distribution. Accordingly, unless specified differently herein, these attributes described herein may be construed as an average value, and in certain embodiments may be construed on "weight average" basis. For example, the term "molecular weight" refers to weight average molecular weight, (Mw). Similarly, references to "average degree of polymerization" and "average carbon chain" length may be calculated on a weight average basis.

Unless defined otherwise, all concentrations refer to concentrations by weight of the sunscreen composition. Also, unless specifically defined otherwise, the term "essentially free of," with respect to a class of ingredients, refers to the particular ingredient(s) being present in a concentration less than is necessary for the particularly ingredient to be effective to provide the benefit or property for which it otherwise would be used, for example, about 1% or less, or about 0.5% or less.

Unless otherwise described, by "UV-absorbing", it is meant a material that absorbs radiation in some portion of the ultraviolet spectrum (wavelengths between 290 and 400 nm), such as one having a molar extinction coefficient of at least about 1000 mol$^{-1}$ cm$^{-1}$, such as at least about 5000, such as at least about 10,000 mol$^{-1}$ cm$^{-}$ for at least one wavelength within the above-defined ultraviolet spectrum. SPF values disclosed and claimed herein are determined using the in-vitro method described herein below.

UV-Absorbing Polyglycerol

Embodiments of the invention relate to sunscreen compositions including a UV-absorbing polyglycerol. UV-absorbing-polyglycerols according to the present invention comprise a UV-absorbing chromophore chemically bound thereto, each as further described and defined herein below. According to certain embodiments, the UV-absorbing polyglycerol, absorbs radiation in some portion of the ultraviolet spectrum (wavelengths between 290 and 400 nm), such as one having a molar extinction coefficient of at least about 1000 mol$^{-1}$ cm$^{-1}$, such as at least about 5000, such as at least about 10,000 mol$^{-1}$ cm$^{-1}$ for at least one wavelength within the above-defined ultraviolet spectrum. The UV-absorbing polyglycerol has a weight average molecular weight ($M_w$) which may be suitable for reducing or preventing the chromophore from absorbing through the skin. According to one embodiment, a suitable molecular weight for the UV-absorbing polyglycerol is $M_w$ greater than 500. In one embodiment, $M_w$ is in the range of about 500 to about 50,000. In another embodiment, $M_w$ is in the range of about 500 to about 5,000. In another embodiment, the $M_w$ is in the range of about 1,000 to about 20,000, such as from about 1,000 to about 10,000.

Described herein is a composition including a UV-absorbing polyglycerol. As one skilled in the art will recognize, "polyglycerol" indicates that the UV-absorbing polymer includes a plurality of glyceryl repeat units covalently bonded to each other. The "backbone" of the UV-absorbing polyglycerol refers to the longest continuous sequence of covalently bonded glyceryl repeat units. Other smaller groups of covalently bonded atoms are considered pendant groups that branch from the backbone.

By "glyceryl repeat units" (also referred to herein as "glyceryl remnant units") it is meant glycerol units excluding nucleophilic groups such as hydroxyl groups. Glyceryl remnant units include ether functional groups, and generally may be represented as $C_3H_5O$ for linear and dendritic remnants (Rokicki et al. *Green Chemistry.*, 2005, 7, 52). Suitable glyceryl remnant units include dehydrated forms (i.e. one mole of water removed) of the following glyceryl units: linear-1,4 ($L_{1,4}$) glyceryl units; linear-1,3 ($L_{1,3}$) glyceryl repeat units; dendritic (D) glyceryl units; terminal-1,2 ($T_{1,2}$) units; and terminal-1,3 ($T_{1,3}$) units. Examples of linear glyceryl remnant units and terminal units are shown below (to the right side of the arrows). The corresponding glyceryl unit before dehydration (shown to the left side of arrows; includes hydroxyls) are shown as well:

linear-1,4 ($L_{1,4}$) glyceryl repeat units

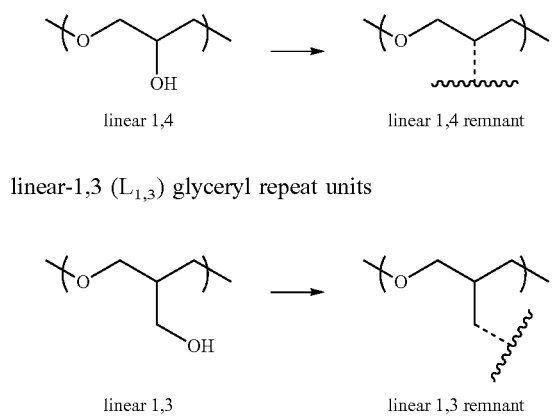

linear-1,3 ($L_{1,3}$) glyceryl repeat units

Those skilled in the art of polymer chemistry will recognize that a polyglycerol, like any typical polymer, is comprised of repeating units and end groups. In the simple case of a polymer formed by condensation of monomer units (elimination of water during polymerization), the end groups are comprised of the parent molecule, while the repeating unit is derived from the parent monomer minus a water molecule. Such is the case for polyglycerols, which can be synthesized by using the monomeric glycerol.

UV-absorbing polyglycerols useful in the present invention may have an average degree of glycerol polymerization that is from about 2 to about 20, such as from about 3 to about 12. This is further illustrated in the Structure I below, where repeating unit isomers have been demarcated by parentheses (7 total glyceryl repeat units) and the terminal glyceryl remnant demarcated by brackets (1 terminal glyceryl remnant), yielding a total degree of polymerization (DP) of 8. The "Z" in Structure I is selected from a UV-absorbing chromophore, a hydrophobic moiety, or an unreacted hydroxyl group.

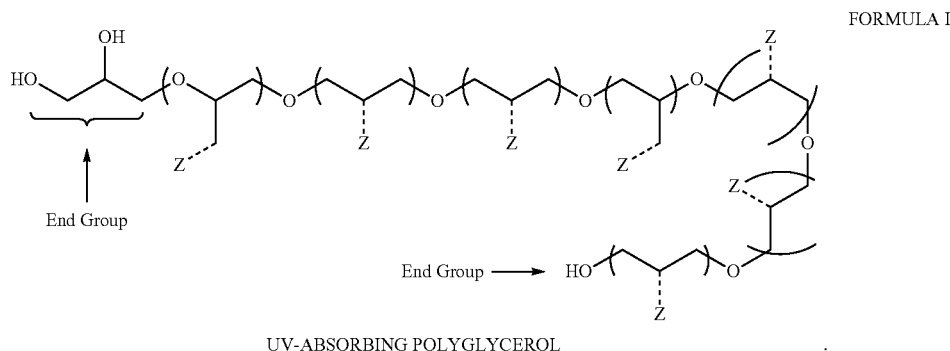

FORMULA I

UV-ABSORBING POLYGLYCEROL terminal-1,2 ($T_{1,2}$) units

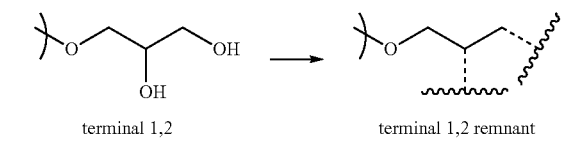

and terminal-1,3 ($T_{1,3}$) units

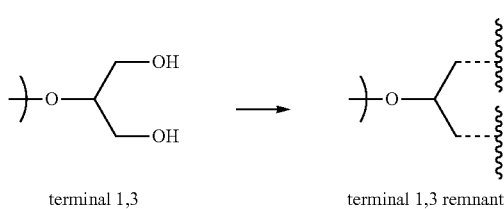

As described above, the polyglycerol may include one or more hydrophobic moieties covalently bound thereto. Suitable hydrophobic moieties include, for example, nonpolar moieties that contain at least one of the following: (a) a carbon-carbon chain of at least six carbons in which none of the six carbons is a carbonyl carbon or has a hydrophilic moiety bonded directly to it; (b) three or more alkyl siloxy groups (—[Si(R)$_2$—O]—); and/or (c) three or more oxypropylene groups in sequence. A hydrophobic moiety may be, or include, linear, cyclic, aromatic, saturated or unsaturated groups. Preferred hydrophobic moieties include 6 or more carbon atoms, more preferably from 8 to 30 carbon atoms, even more preferably from 10 to 26 carbon atoms, and most preferably from 12 to 24 carbon atoms. Examples of hydrophobic moieties include linear or branched, saturated or unsaturated alkyl moieties, e.g. linear or branched, saturated or unsaturated $C_8$-$C_{30}$ alkyl, such as decyl, undecyl, dodecyl(lauryl), tridecyl, tetradecyl(myristyl), pentadecyl, hexadecyl(cetyl, palmityl), heptadecyl, heptadecenyl, hepta-8-decenyl, hepta-8,11-decenyl, octadecyl (stearyl), nonadecyl, eicosanyl, henicosen-12-yl, henicosanyl, docosanyl(behenyl), and the like as well as benzyl. Certain preferred hydrophobic moieties include heptadecyl, heptadecenyl, hepta-8-decenyl, hepta-8,11-decenyl and the like. Other examples of hydrophobic moieties include groups such as poly(oxypropylene), poly(oxybutylene), poly(dimethylsiloxane), and fluorinated hydrocarbon groups containing a carbon chain of at least six carbons in which none of the six carbons has a hydrophilic moiety bonded directly to it, and the like.

According to certain embodiments, polymer compositions of the present invention include low fractions of diglycerol chromophore conjugates. By "diglycerol chromophore conjugates," it is meant polyglycerols having two glyceryl repeat units and at least one UV-chromophore chemically-bound thereto, including the dehydrated forms. An example structure is shown below in FORMULA II

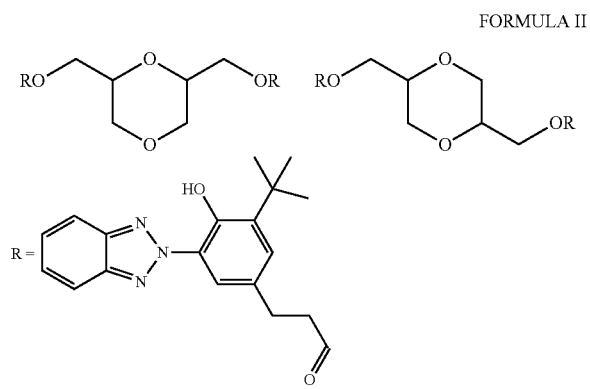

FORMULA II

By "low fractions" of diglycerol chromophore conjugates, it is meant that that the valley-to-valley peak area of peaks assignable to diglycerol chromophore conjugates in the ultraviolet radiation absorbing polyglycerol comprises about 1 percent or less of the total valley-to-valley peak area of all peaks in the spectrogram, i.e. "total peak area", such as about 0.5 percent or less of the total peak area, such as about 0.2 percent or less of the total peak area, as determined by chromatogram analysis, as set forth in the Examples below.

As one skilled in the art will readily recognize, one particularly suitable method for generating a chromatogram for determining the relative presence of chemical structures in a polymer composition involves the use of high performance liquid chromatography (HPLC), ultraviolet/visible (UV-VIS) and mass spectrometry (MS). For example, the polymer composition may be tested for component analysis by separating components using HPLC. Detection is performed using ultraviolet/visible (UV-VIS) and mass spectrometry (MS) to generate a chromatogram of peaks at particular retention times, which peaks are assigned to individual components. According to certain embodiments of the invention, such analysis reveals no peak assignable to diglycerol chromophore conjugates. According to certain other embodiments, if such a peak exists, one skilled in the art will readily appreciate that the total peak area can be ascertained by connecting adjacent minima of points on the chromatogram and calculating (integrating) area under the curve for each of the various peaks. A specific suitable HPLC method for assessing the presence of diglycerol conjugates is provided below.

Polyglycerols described herein can be obtained through various synthetic routes. One particularly suitable route includes preparing a polyglycerol intermediate by polymerizing glycerol, such as by combining glycerol and suitable reactant such as an inorganic base (alkali) into a reactor and applying vacuum, agitation and heat in order to facilitate the polymerization of glycerol. By utilizing this method, glycerol is polymerized in a controlled fashion which tends to produce high polyglycerol intermediates with high linearity (less cyclic). According to one particular embodiment, the reactant is a multivalent inorganic base, such as a calcium-containing compound, such as calcium hydroxide. The temperature of the reactor may be maintained, for example between 200° C. and 240° C., such as 220° C. and 240° C. Suitable pressures may be from about 10 mm Hg to about 400 mm Hg, such as from about 100 mm Hg to about 400 mm Hg, such as about 150 mm Hg. Suitable molar ratios of glycerol to calcium-containing compound range from about 1:0.0002 to about 1:0.005.

According to certain embodiments, the polyglycerol intermediate is reacted with a hydrophobic reactant. Suitable hydrophobic reactants are those that are capable of displacing hydroxyl groups on the polyglycerol intermediate and covalently bonding thereto in order to ultimately provide a hydrophobic moiety (described above) bound to the UV-absorbing polyglycerol. As one skilled in the art will readily appreciate, suitable examples of hydrophobic reactants include linear or branched, saturated or unsaturated $C_8$-$C_{30}$ fatty acids, capable of reacting with hydroxyls on the polyglycerol intermediate and attaching to the polyglycerol via an ester linkage, $C_8$-$C_{30}$ isocyanates capable of reacting with hydroxyls via a urethane linkage. Other suitable hydrophobic reactants include $C_8$-$C_{30}$ epoxides, $C_8$-$C_{30}$ halohydrins, $C_8$-$C_{30}$ alkyl halides, among other hydrophobic reactants capable of condensation reactions with pendant hydroxyls on the polyglycerol intermediate. In this embodiment, a hydrophobically-modified polyglycerol intermediate is formed.

According to certain embodiments, the polyglycerol intermediate (or hydrophobically-modified polyglycerol intermediate) is enriched, i.e. residual glycerol and low molecular weight (low DP) fractions of polyglycerol are removed from the polyglycerol intermediate to form an enriched polyglycerol intermediate. Residual glycerol may be removed, for example, by heating and applying a vacuum. Suitable conditions for removing unreacted glycerol may be a temperature of about 200° C. and pressure of about 4 mm Hg. Additional glycerol may be removed by introducing steam through the bottom of the reactor One particularly suitable method of removing glycerol as well as low DP components such as diglycerol includes applying heat and vacuum to the polyglycerol intermediate while the polyglycerol intermediate is drawn into a thin film. This so-called "wiped film evaporation" includes providing the polyglycerol intermediate to a chamber having a heated surface, applying vacuum, spreading thin films of the polyglycerol intermediate across the heated surface to selectively evaporate low molecular weight fractions of the polyglycerol intermediate. Spreading of the polyglycerol intermediate may be performed mechanically, such as via flexible blades that rotate about an axis and within the chamber, drawing the fluid polyglycerol intermediate into a film and facilitating evaporation and removal of fractions that are desirably removed, to form an enriched polyglycerol intermediate. Temperatures may be held at about 260° C. and pressures at about 10 to 50 millitorr.

Suitable UV-absorbing chromophores that may be chemically bound in UV-absorbing polyglycerols of the present invention in order to render them UV-absorbing include aromatic ring structures with UV-absorbing chromophores chemically attached thereto (a moiety containing a five-membered heterocyclic ring with two carbon and three nitrogen atoms). Examples of UV-absorbing chromophores include, but are not limited to, triazoles, such as benzotriazoles and triazines. In one embodiment, the UV-absorbing chromophore of Formulas I and II includes a pendant UV-absorbing triazine (a six membered heterocycle containing three nitrogen and three carbon atoms). Suitable UV-absorbing chromophores include those that have absorbance of UVA radiation. Other suitable UV-absorbing chromophores are those which have absorbance in the UVB region. In another embodiment, the UV-absorbing chromophore absorbs in both the UVA and UVB region. In yet another embodiment, when the UV-absorbing polyglycerol is cast into a film, it is possible to generate a molar extinction coefficient measured for at least one wavelength in this wavelength range of at least about 1000 mol$^{-1}$ cm$^{-1}$, preferably at least about 2000 mol$^{-1}$ cm$^{-1}$, more preferably at least about 4000 mol$^{-1}$ cm$^{-1}$. In one embodiment, the molar extinction coefficient among at least 40% of the wavelengths in this portion of the spectrum is at least about 1000 mol$^{-1}$ cm$^{-1}$. Examples of UV-chromophores that are UVA absorbing include triazoles such as benzotriazoles, such as hydroxyphenyl-benzotriazoles; camphors such as benzylidene camphor and its derivatives (such as terephthalylidene dicamphor sulfonic acid); dibenzoylmethanes and their derivatives.

In one embodiment, the UV-absorbing chromophore is a benzotriazole providing both photostability and strong UVA absorbance with a structure represented in FORMULA III.

FORMULA III

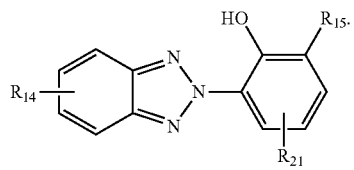

BENZOTRIAZOLE UV-ABSORBING CHROMOPHORE wherein each R$_{14}$ is independently selected from the group consisting of hydrogen, C$_1$-C$_{20}$ alkyl, alkoxy, acyl, alkyloxy, alkylamino, and halogen; R$_{15}$ is independently selected from the group consisting of hydrogen, C$_1$-C$_{20}$ alkyl, alkoxy, acyl, alkyloxy, and alkylamino, R$_{21}$ is selected from C$_1$-C$_{20}$ alkyl, alkoxy, acyl, alkyloxy, and alkylamino. Either of the R$_{15}$ or R$_{21}$ groups may include the remnants of functional groups after reaction between the UV-absorbing chromophore and the enriched polyglycerol intermediate. In one embodiment, the UV-absorbing triazole is derived from a transesterification product of 3-(3-(2H-benzo[d][1,2,3]triazol-2-yl)-5-(tert-butyl)-4-hydroxyphenyl)propanoic acid with polyethylene glycol 300, commercially available as TINUVIN 213, also available from BASF. In another embodiment, the UV-absorbing triazole is Benzenepropanoic acid, 3-(2H-benzotriazol-2-yl)-5-(1,1-dimethylethyl)-4-hydroxy-, C$_{7-9}$-branched and linear alkyl esters, commercially available as TINUVIN 99, also available from BASF. In another embodiment, the UV-absorbing group contains a triazine moiety. An exemplary triazine is 6-octyl-2-(4-(4,6-di([1,1'-biphenyl]-4-yl)-1,3,5-triazin-2-yl)-3-hydroxyphenoxy)propanoate (a compound sold under the trade name TINUVIN 479 by BASF Corporation, Wyandotte, Mich.).

In another embodiment, the UV-absorbing chromophore is a UVB-absorbing moiety. By UVB-absorbing chromophore it is meant that the UV-absorbing chromophore has absorbance in the UVB portion (290 to 320 nm) of the ultraviolet spectrum. In one embodiment, the criteria for consideration as a UVB-absorbing chromophore is similar to those described above for an UVA-absorbing chromophore, except that the wavelength range is 290 nm to 320 nm. Examples of suitable UVB-absorbing chromophores include 4-aminobenzoic acid and alkane esters thereof; anthranilic acid and alkane esters thereof; salicylic acid and alkane esters thereof; hydroxycinnamic acid alkane esters thereof; dihydroxy-, dicarboxy-, and hydroxycarboxybenzophenones and alkane ester or acid halide derivatives thereof; dihydroxy-, dicarboxy-, and hydroxycarboxychalcones and alkane ester or acid halide derivatives thereof; dihydroxy-, dicarboxy-, and hydroxycarboxycoumarins and alkane ester or acid halide derivatives thereof; benzalmalonate (benzylidene malonate); benzimidazole derivatives (such as phenyl benzilimazole sulfonic acid, PBSA), benzoxazole derivatives, and other suitably functionalized species capable of being covalently bonded within the polymer chain. In another embodiment, the UV-absorbing polyglycerol includes more than one UV-absorbing chromophore, or more than one chemical class of UV-absorbing chromophore.

According to certain embodiments of the invention, in order to provide a chemically bound UV-absorbing chromophore on UV-absorbing polyglycerols present in polymer compositions of the present invention, a "post-polymerization attachment" technique may be employed. Unreacted, pendant hydroxyl groups present in the polyglycerol intermediate are reacted with a UV-absorbing chromophore containing a complementary functional group to obtain a UV-absorbing polyglycerol. Suitable complementary functional groups on UV-absorbing chromophores include carboxylates, isocyanates, epoxides, esters, alkyl esters, acid halides, and the like. One example of a UV-absorbing chromophore having complementary functional groups is a benzotriazole carboxylate UV-absorbing chromophore, 3-(3-(2H-benzo[d][1,2,3]triazol-2-yl)-5-(tert-butyl)-4-hydroxyphenyl)propanoic acid, shown below in FORMULA IV and its ester derivative, polyethylene glycol ester of 3-[3-(2H-1,2,3-benzotriazol-2-yl)-5-tert-butyl-4-hydroxyphenyl]propanoate

FORMULA IV

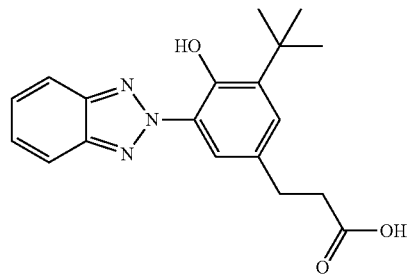

4

In this embodiment, the pendant hydroxyls on the enriched polyglycerol intermediate react via condensation with the complementary carboxylate functional group on the UV-absorbing chromophore. Benzotriazoles having carboxylate or other complementary functional groups may be prepared using methods known to those skilled in the art, such as those described in published U.S. patent application 2012/0058974, "Composition Comprising Pesticide and Benzotriazole UV Absorbers," which is herein incorporated by reference in its entirety.

Polymer compositions formed via these methods are accordingly the reaction product of enriched polyglycerol intermediate or, alternatively, a hydrophobically modified polyglyerol, such as a polyglycerol ester, and a UV-absorbing chromophore having a functional group suitable for covalent attachment to the polyglycerol intermediate.

According to one specific embodiment, a polyglycerol intermediate is formed by polymerizing glycerol by reacting glycerol with calcium hydroxide. The temperature of the reactor is maintained between 200° C. and 240° C., and pressure is maintained at about 400 mm Hg and using a molar ratio of glycerol to calcium hydroxide from about 1:0.0002 to about 1:0.005. Residual glycerol and low molecular weight polyglycerols are removed using a wiped film evaporator having a barrel temperature of about 260° C. and pressures at about 10 to 50 millitorr, thereby forming an enriched polyglycerol intermediate. The enriched polyglycerol intermediate is optionally esterified with stearic acid at elevated temperature (about 250° C.) for several hours until clear, to form a hydrophobically-modified polyglycerol intermediate. Excess hydroxide is neutralized with phosphoric acid.

A benzotriazole carboxylate may be prepared by adding, for example, the polyethylene glycol ester of 3-[3-(2H-1,2, 3-benzotriazol-2-yl)-5-tert-butyl-4-hydroxyphenyl]propanoate (a chromophore sold under the trade name TINUVIN 213 by BASF Corporation, Wyandotte, Mich.). 81.0 g is added to a 2 L round bottom flask containing a magnetic stir bar. Ethanol (600 mL) is added to the flask by funnel, and the mixture is stirred until homogeneous. Sodium hydroxide (NaOH, 30.8 g) is dissolved in $H_2O$ (400 mL); the basic solution is transferred into an addition funnel above the 2 L flask. The NaOH solution is added slowly to the stirred mixture. When addition is complete, the mixture is stirred overnight at room temperature. The solution is concentrated by rotary evaporation to remove most of the ethanol. The resulting orange oil is diluted to 1400 mL with $H_2O$. The mixture is stirred mechanically and acidified to ~pH 1 by addition of 1 M aq. HCl (~700 mL). The resulting white precipitate is filtered and pressed to remove water, then recrystallized from ethanol. The supernatant is removed and concentrated by rotary evaporation; a second crop of material is isolated as a white, amorphous solid. The two crops are combined and dried in a vacuum oven overnight to form a benzotriazole carboxylate.

The enriched, hydrophobically-modified polyglycerol is reacted with the benzotriazole carboxylate (8.8 g, 23.8 mmol) by transferring into a 2-neck 100 mL round bottom flask containing a magnetic stir bar. The flask is fitted with a nitrogen inlet adapter and distillation adapter with 100 mL receiving flask. The apparatus is placed under vacuum for one hour, then backfilled with nitrogen. The distillation head is removed, and tin (II) ethyl hexanoate (50 µL) is added to the reaction flask by syringe under nitrogen flow. The apparatus is reassembled, then purged under vacuum and backfilled with nitrogen 3 times. The reaction flask is immersed in an oil bath that was warmed to 180° C. with constant flow of nitrogen into the 2-neck flask through the distillation adapter and out of the vacuum adapter to room atmosphere. The reaction is stirred for three hours and then cooled to room temperature under nitrogen flow, affording the product, a polymer composition including UV-absorbing polyglycerol, as a yellow solid.

As one skilled in the art will recognize, the UV-absorbing polyglycerols that are useful in topical compositions of the present invention are prepared via polymer synthesis. Synthesis of the UV-absorbing polyglycerol generally results in a reaction product, hereinafter referred to as a "polymer composition", that is a mixture of various molecular weights of UV-absorbing polyglycerols. Despite the removal/reduction of glycerol and low-molecular glycerol conjugates, the polymer composition may further include (apart from the UV-absorbing polyglycerol composition) a small amount of unbound, i.e. unconjugated, material, e.g., glycerol, chromophore or hydrophobic moieties that are not covalently bound to the polyglycerol backbone.

According to certain embodiments, the polymer composition to be incorporated into topical compositions of the present invention comprises about 90% or more of the UV-absorbing polyglycerol. According to certain other embodiments, the polymer composition comprises about 95% or more of the UV-absorbing polyglycerol. According to certain other embodiments, the polymer composition comprises about 98% or more of the UV-absorbing polyglycerol, such as about 99% or more.

Sunscreen compositions described herein are useful for topical application where reducing exposure of the human body to UV radiation is desired. Sunscreen compositions described herein may be prepared using conventional methods, such as by blending the polymer composition with the cosmetically acceptable carrier, and other optional ingredients. The incorporation of UV-absorbing polyglycerols and non-UV-absorbing polyglycerols into such compositions of the present invention may provide enhanced SPF (primarily UVB absorbance), enhanced PFA (primarily UVA absorbance) or enhancement of both. As such, the polymer composition may be formulated using ingredients known in the art into a spray, lotion, gel, stick or other product forms. Similarly, according to certain embodiments, one may protect human skin from UV radiation by topically applying a composition comprising the polymer composition containing the UV-absorbing polyglycerol.

According to certain embodiments, a UV-absorbing sunscreen agent present in topical compositions of the present invention may consist of, or consist essentially of, the UV-absorbing polyglycerol. According to certain other embodiments, the UV-absorbing sunscreen agent may include additional UV-absorbing polymers, other than those UV-absorbing polyglycerols, as defined herein, and/or non-UV-absorbing, light-scattering particles. Additional UV-absorbing polymers are molecules that can be represented as having one or more structural units that repeat periodically, e.g., at least twice, to generate the molecule.

In certain embodiments, the topical compositions may be essentially free of UV-absorbing polymers other than the UV-absorbing polyglycerols. By "essentially free of UV-absorbing polymers other than the UV-absorbing polyglycerols", it is meant that the compositions do not contain UV-absorbing polymers other than the UV-absorbing polyglycerols in an amount effective to provide the compositions with an SPF of greater than 2 in the absence of the UV-absorbing polyglycerol and non-polymeric UV-absorbing sunscreen agents. In yet other embodiments, the compositions may be essentially free of both UV-absorbing polymers other than the UV-absorbing polyglycerols and non-polymeric UV-absorbing sunscreen agents, as described below. For example, the compositions of the invention will contain about 1% or less, or about 0.5% or less, of such UV-absorbing polymers other than the UV-absorbing polyglycerols and/or such non-polymeric UV-absorbing sunscreen agents.

Additional UV-absorbing polymers may have a molecular weight of greater than about 1500. Examples of suitable additional UV-absorbing polymers include benzylidene malonate silicone, including those described in U.S. Pat. No. 6,193,959, to Bernasconi et al. A particularly suitable benzylidene malonate includes "Parsol SLX," commercially available from DSM (Royal DSM N.V.) of Heerlen, Netherlands. Other suitable additional UV-absorbing polymers are disclosed in U.S. Pat. Nos. 6,962,692; 6,899,866; and/or U.S. Pat. No. 6,800,274; including hexanedioic acid, polymer with 2,2-dimethyl-1,3-propanediol, 3-[(2-cyano-1-oxo-3,3-diphenyl-2-propenyl)oxy]-2,2-dimethylpropyl 2-octyl-dodecyl ester; sold under the trade name "POLYCRYLENE," commercially available from the Hall-Star Company of Chicago, Ill. When utilized, such additional UV-absorbing polymers may be used at concentrations of about 1% or more, for example about 3% or more.

Non-UV-absorbing, light-scattering particles do not absorb in the UV spectrum, but may enhance SPF by scattering of the incident UV radiation. Examples of non-UV-absorbing, light-scattering particles include solid particles having a dimension, e.g., average diameter, from about 0.01 micron to about 10 microns. In certain embodiments, the non-UV-absorbing, light-scattering particle is a hollow particle comprising, or consisting essentially of, an organic polymer or a glass. Suitable organic polymers include acrylic polymers, including acrylic/styrene copolymers, such as those known as SUNSPHERES, which are commercially available from Dow Chemical of Midland, Mich. Suitable glasses include borosilicate glasses such as those described in published United States Patent Application US20050036961A1, entitled, "AESTHETICALLY AND SPF IMPROVED UV-SUNSCREENS COMPRISING GLASS MICROSPHERES".

Non-UV-Absorbing Polyglycerol

"Non-UV-absorbing" polyglycerol, according to certain embodiments, refers to polyglycerols (as defined above—as includes a plurality of glyceryl repeat units covalently bonded to each other), which do not absorb radiation appreciably in the ultraviolet spectrum (290 nm-400 nm). Suitable non-UV-absorbing polyglycerols may have a molar extinction coefficient of less than about 1000 mol$^{-1}$ cm$^{-1}$ for 95% or more wavelengths in the spectral region noted above, such as less than about 500 mol$^{-1}$ cm$^{-1}$ for wavelengths in the spectral region noted above. According to certain other embodiments, the non-UV-absorbing polyglycerols are free of chemically bound aromatic ring structures, such as those that would otherwise render the polyglycerol UV-absorbing, as defined herein.

The non-UV-absorbing polyglycerol may have an average degree of (glycerol) polymerization that is from about 2 to about 20, such as from about 3 to about 12. According to certain embodiments the average degree of (glycerol) polymerization may be similar to the average degree of glycerol polymerization of the UV-absorbing polyglycerol. For example, the average degree of glycerol polymerization of the UV-absorbing polyglycerol and the average degree of glycerol polymerization of the non-UV-absorbing polyglycerol may be within about 2 units, such as within about 1 unit.

The non UV-absorbing polyglycerols suitable for use in the present invention generally comprise one or more glycerol repeat units having pendant hydroxyl groups. One or more these pendant hydroxyl groups may be reacted with a hydrophobic reactant in order to provide one or more hydrophobic moieties covalently bound thereto. Suitable hydrophobic moieties include those discussed above with references to hydrophobic moieties that may be included on the UV-absorbing polyglycerol. Suitable hydrophobic reactants are those that are capable of displacing hydroxyl groups on the polyglycerol intermediate and covalently bonding thereto in order to ultimately provide a hydrophobic moiety (described above) bound to the non-UV-absorbing polyglycerol. As one skilled in the art will readily appreciate, suitable examples of hydrophobic reactants include linear or branched, saturated or unsaturated $C_8$-$C_{30}$ fatty acids, capable of reacting with hydroxyls on the polyglycerol intermediate and attaching to the polyglycerol via an ester linkage, $C_8$-$C_{30}$ isocyanates capable of reacting with hydroxyls via a urethane linkage. Other suitable hydrophobic reactants include $C_8$-$C_{30}$ epoxides, $C_8$-$C_{30}$ halohydrins, $C_8$-$C_{30}$ alkyl halides, among other hydrophobic reactants capable of condensation reactions with pendant hydroxyls on the non-UV absorbing polygylcerol.

Specific examples of non-UV-absorbing polyglycerols include polyglycerol esters of various fatty acids, sold by LONZA Group of Basel, Switzerland under the POLY-ALDO trade name. According to certain embodiments, both the UV-absorbing polyglycerol and the non-UV-absorbing polyglycerol each include hydrophobic moieties covalently bound thereto. The number of carbon atoms in the hydrophobic moiety of the UV-absorbing polyglycerol may be similar to the number of carbon atoms in the hydrophobic moiety of the non UV-absorbing polyglycerol. For example, the UV-absorbing polyglycerol may include a first hydrophobic moiety and non UV-absorbing polyglycerol may include a second hydrophobic moiety. The first hydrophobic moiety may have a first average number of carbon atoms and the second hydrophobic moiety may have a second average number of carbon atoms. The first average number of carbon atoms and said second average number of carbon atoms are within 10 carbon atoms of one another, such as within 6 carbon atoms of one another, such as within 2 carbon atoms of one another.

According to certain embodiments, the sum of the concentration by weight of the UV-absorbing polyglycerol and the concentration by weight of the non-UV-absorbing polyglycerol may be about 12 percent or more, such as about 15 percent or more, preferably about 20 percent or more, such as about 25 percent or more. According to certain other embodiments, the concentration by weight of the UV-absorbing polyglycerol is about ten percent or more and the concentration by weight of the non-UV-absorbing polyglycerol is about 2 percent or more.

Topical Composition

In one embodiment, a composition suitable for topical/cosmetic use for application to the human body, e.g., keratinaceous surfaces such as the skin, hair, lips, or nails, and especially the skin, is provided. The composition includes the polymer composition comprising the UV-absorbing polyglycerols that comprise a UV-chromophore chemically bound thereto.

As discussed above, the concentration of the UV-absorbing polyglycerol comprise a UV-chromophore chemically bound thereto in the topical composition may be sufficient to provide an SPF of about 10 or greater, particularly where the composition is free of, or essentially free of, additional UV-absorbing polymers other than the UV-absorbing polyglycerols, or non-polymeric UV-absorbing sunscreen agents as described herein. Accordingly, the concentration of the UV-absorbing polyglycerol may vary from about 5% to about 50%, such as from about 7% to about 40%, such as from about 10% to about 30%, such as from about 15% to about 30% of the composition. In certain embodiments, the concentration of UV-absorbing polyglycerol is about 10% or more, such as about 15% or more, such about 25% or more of the composition. According to certain embodiments where the sunscreen agent consists essentially of the UV-absorbing polyglycerol, the concentration of the UV-absorbing polyglycerol may be about 15% or more.

The concentration of non-UV-absorbing light scattering particles, if present, may be about 1% or more, such as from about 1% to about 10%, such as from about 2% to about 5%. In certain embodiments where the UV-sunscreen agent further includes a non-UV-absorbing sunscreen agent in amounts as discussed above, compositions of the present invention may have an SPF of about 20 or greater.

Compositions of the present invention, according to certain embodiments, may be essentially free of non-polymeric UV-absorbing sunscreen agents. By "essentially free of non-polymeric UV-absorbing sunscreen agents," it is meant that, in this embodiment, the compositions do not contain non-polymeric UV-absorbing sunscreen agents in an amount effective to provide the compositions with an SPF of greater than 2 in the absence of the UV-absorbing polyglycerol and UV-absorbing polymers other than the UV-absorbing polyglycerols used in the present invention, as determined via the in vitro method described herein below. For example, the compositions of the invention will contain about 1% or less, or about 0.5% or less, of such non-polymeric UV-absorbing sunscreen agents. One example of non-polymeric UV-absorbing sunscreen agents that the composition is essentially free of typically may be characterized as "organic" (include predominantly or only atoms selected from carbon, hydrogen, oxygen, and nitrogen) and having no definable repeat unit and typically having molecular weights that are about 600 daltons or less, such as about 500 daltons or less, such as less than 400 daltons. Examples of such compounds, sometimes referred to as "monomeric, organic UV-absorbers" include, but are not limited to: methoxycinnamate derivatives such as octyl methoxycinnamate and isoamyl methoxycinnamate; camphor derivatives such as 4-methyl benzylidene camphor, camphor benzalkonium methosulfate, and terephthalylidene dicamphor sulfonic acid; salicylate derivatives such as octyl salicylate, trolamine salicylate, and homosalate; sulfonic acid derivatives such as phenylbenzimidazole sulfonic acid; benzone derivatives such as dioxybenzone, sulisobenzone, and oxybenzone; benzoic acid derivatives such as aminobenzoic acid and octyldimethyl para-amino benzoic acid; octocrylene and other β,β-diphenylacrylates; dioctyl butamido triazone; octyl triazone; butyl methoxydibenzoyl methane; drometrizole trisiloxane; bis-ethylhexyloxyphenol methoxyphenyl triazine and menthyl anthranilate.

Other non-polymeric UV-absorbing sunscreen agents that the composition may be essentially free of may include ultraviolet-absorbing particles, such as certain inorganic oxides, including titanium dioxide, zinc oxide, and certain other transition metal oxides. The compositions may also be essentially free of organic particulates such as Tinosorb M. Such ultraviolet screening particles are typically solid particles having a diameter from about 0.1 micron to about 10 microns.

In yet other embodiments the compositions may include one percent or more of such non-polymeric UV-absorbing sunscreen agents, for example greater than 10 percent of non-polymeric UV absorbing sunscreen agents. The non-polymeric UV absorbing agents may be selected from inorganic particulates, organic particulates, polymerics, or organics.

The compositions of the present invention may be used for a variety of cosmetic uses, especially for protection of the skin from UV radiation. The compositions, thus, may be made into a wide variety of delivery forms. These forms include, but are not limited to, suspensions, dispersions, solutions, or coatings on water soluble or water-insoluble substrates (e.g., substrates such as organic or inorganic powders, fibers, or films). Suitable product forms include lotions, creams, gels, sticks, sprays, ointments, mousses, and compacts/powders. The composition may be employed for various end-uses, such as recreation or daily-use sunscreens, moisturizers, cosmetics/make-up, cleansers/toners, anti-aging products, or combinations thereof. The compositions of the present invention may be prepared using methodology that is well known by an artisan of ordinary skill in the field of cosmetics formulation.

Topical Carrier

The one or more UV-absorbing polymers in the composition may be combined with a "cosmetically-acceptable topical carrier," i.e., a carrier for topical use that is capable of having the other ingredients dispersed or dissolved therein, and possessing acceptable properties rendering it safe to use topically. As such, the composition may further include any of various functional ingredients known in the field of cosmetic chemistry. For example, the sunscreen composition may include one, two, three or more of the following classes of materials: hydrophobic diluents, $C_2$-$C_3$ mono-alcohol, glycols or other humectants, emulsifiers, thickeners, opacifiers, fragrances, dyes, film-forming polymers, preservatives, among other functional ingredients.

Hydrophobic diluents include compounds that are suitable for providing emolliency and, in certain embodiments for solublizing the UV-absorbing polyglycerol. Suitable hydrophobic diluents include those compounds generally insoluble in water and may fall into one or more of the following classes: (a) has a carbon chain of at least four carbons in which none of the four carbons is a carbonyl carbon; (b) has two or more alkyl siloxy groups; or (c) has two or more oxypropylene groups in sequence. The hydrophobic diluents may include linear, cyclic, aromatic, saturated or unsaturated groups and may be any of various hydrocarbons (straight or branched chain alkanes or alkenes, ketone, diketone, primary or secondary alcohols, aldehydes, sterol esters, alkanoic acids, turpenes, monoesters), such as those having a carbon chain length ranging from $C_6$-$C_{38}$, such as $C_6$-$C_{18}$. In one embodiment of the invention, the oils include ester and/or ether functional groups.

According to certain embodiments, compounds that are amphiphilic are excluded from the definition of "oil" and such compounds that have hydrophilic moieties, such as anionic, cationic, zwitterionic, or nonionic groups, that are polar, including sulfate, sulfonate, carboxylate, phosphate, phosphonates, ammonium, including mono-, di-, and trialkylammonium species, pyridinium, imidazolinium, amidinium, poly(ethyleneiminium), ammonioalkylsulfonate, ammonioalkylcarboxylate, amphoacetate, and poly(ethyleneoxy)sulfonyl moieties, are so excluded.

The hydrophobic diluent may be an oil, e.g., may be a hydrophobic compound with a melting point that is below 30° C. and insoluble in water. Examples include alkyl diesters, such as diisopropyl adipate, available as CRODAMOL DA from Croda Inc. of Edison, N.J.; a reaction product of a glycol and a fatty acid, such as a PPG-2 myristyl ether propionate available as Crodamol PMP from Croda Inc. of Edison, N.J.; a triglyceride such as a mixture of caprylic/capric triglycerides, available as MIGLYOL 812 from Sasol Olefins & Surfactants of Houston, Tex.; an alkyl fatty acid ester such as isopropyl palmitate, available as PROPAL NF from the Lubrizol Corporation of Wickliffe, Ohio; an alkyl benzoate ester such as a $C_{12}$-$C_{18}$ alkyl benzoate, available as FINSOLV TN; an alkyl carbonate ester such as a dialkyl carbonate such as dicaprylyl carbonate, available as CETIOL CC from Cognis Corp. of Ambler, Pa.; diethylhexylcyclohexane available as CETIOL S from Cognis; dimethicone and other silicone oils; and mineral oil.

The hydrophobic diluent may be a wax; e.g., a hydrophobic compound with a melting point that is above 30° C., such as between about 30° C. and 120° C. and insoluble in water. Suitable waxes include any of various hydrocarbons (straight or branched chain alkanes or alkenes, ketone, diketone, primary or secondary alcohols, aldehydes, sterol esters, alkanoic acids, turpenes, monoesters), such as those having a carbon chain length ranging from $C_{12}$-$C_{38}$. Also suitable are diesters or other branched esters. In one embodiment, the compound is an ester of an alcohol (glycerol or other than glycerol) and a $C_{18}$ or greater fatty acid.

Non-limiting examples include any of various natural waxes including lotus wax (e.g., Nelumbo Nucifera Floral Wax available from Deveraux Specialties, Silmar, Calif.); beeswax (e.g., White Beeswax SP-422P available from Strahl and Pitsch of West Babylon, N.Y.), insect waxes, sperm whale oil, lanolin, vegetable waxes such as canauba wax, jojoba oil, candelilla wax; mineral waxes such as paraffin wax; and synthetic waxes such as cetyl palmitate, lauryl palmitate, cetostearyl stearate, and polyethylene wax (e.g., PERFORMALENE 400, having a molecular weight of 450 and a melting point of 84° C., available from New Phase Technologies of Sugar Land, Tex.); and silicone waxes such as $C_{30-45}$ Alkyl Methicone and $C_{30-45}$ Olefin (e.g., Dow Corning AMS-C30, having a melting point of 70° C., available from Dow Corning of Midland, Mich.).

The amount of hydrophobic diluents may be present in the composition from about 2% to about 80%, such as from about 5% to about 60%, or from about 6% to about 40%, such as from about 10% to about 35%.

The vehicle may optionally include a $C_2$-$C_3$ mono-alcohol such as ethanol or isopropanol; or glycols such as glycerin, propylene glycol, and the like.

Furthermore, the composition may be essentially free of ingredients that would render the composition unsuitable for topical use. As such, the composition may be essentially free of solvents such as volatile solvents, and, in particular, free of volatile organic solvents such as ketones, xylene, toluene, and the like.

Sun protection factor (SPF) may be tested using the following IN-VITRO SPF TEST METHOD. The baseline transmission of a PMMA plate (substrate) without application of any test materials applied thereto was measured. Test samples were prepared by providing a sample of polymer. Blends may also be tested by this method. The polymer(s) can be tested without any additional additives; with a solvent system, or as a part of a personal care composition that may include solvent and/or additional ingredients.

Each sample is separately applied to a HD6 PMMA plate (5 cm×5 cm) (available from Helioscience, Marseille, France) using an application density of about 1.3 mg/cm2 or 32.5 mg, rubbing into a uniform thin layer with the operator's finger specifically with North 100 series finger cot, and allowing to dry. The samples are allowed to dry for 15 20 minutes in the dark and ambient temperature before measurement of absorbance using calibrated Labsphere® UV-1000S UV transmission analyzer or a Labsphere® UV-2000S UV transmission analyzer (Labsphere, North Sutton, N.H., USA). The absorbance measures are used to calculate SPF and PFA indices. SPF and PFA may be calculated using methods known in the art—see equation (1) below for calculation of SPF:

$$SPF_{in\ vitro} = \frac{\int_{\lambda=290\ nm}^{\lambda=400\ nm} E(\lambda) * I(\lambda) d\lambda}{\int_{\lambda=290\ nm}^{\lambda=400\ nm} E(\lambda) * I(\lambda) * 10^{-A_0(\lambda)} * d\lambda} \quad (1)$$

where:
$E(\lambda)$=Erythema action spectrum
$I(\kappa)$=Spectral irradiance received from the UV source
$A0(\lambda)$=Mean monochromatic absorbance of the test product layer before UV exposure
$d\lambda$=Wavelength step (1 nm)

The compositions of the present invention may be prepared using mixing and blending methodology that is well known by an artisan of ordinary skill. In one embodiment of the invention, a method of making a composition of the present invention includes preparing an oil phase by mixing at least the UV-absorbing polyglycerol with optional oil-soluble or oil-miscible ingredients; and preparing a water phase, by mixing water and optional water-soluble or water-miscible ingredients. The oil phase and the water phase may then be mixed in a manner sufficient to homogeneously disperse the oil phase in the water phase such that the water phase is continuous and the oil phase discontinuous.

The compositions of the present invention can be used by topically administering to a mammal, e.g., by the direct laying on, wiping or spreading of the composition on the skin or hair of a human.

The following examples are illustrative of the principles and practice of this invention, although not limited thereto. Numerous additional embodiments within the scope and spirit of the invention will become apparent to those skilled in the art once having the benefit of this disclosure.

EXAMPLES

Example 1

Varying weight percentages of UV-absorbing polyglycerol (UVAP) were mixed with a non UV-absorbing polyglycerol (NUVAP), and a carrier that included an oil, water, thickener and emulsifier, to form eight different compositions. The non UV-absorbing polyglycerol was POLYALDO 10-1-S. The oil was CETIOL CC. The thickener was COSMEDIA ATH. COSMEDIA ATH is sodium polyacrylate, ethylhexyl stearate and trideceth-6. The emulsifier was ARLACEL 165 VEG. ARLACEL 165 VEG is glyceryl stearate and PEG-100 stearate. The UV-absorbing polyglycerol was formed by reacting benzotriazole carboxylate with POLYALDO 10-1-S. The formula composition is described below in Table 1. The UV-absorbing polyglycerol was dissolved in CETIOL CC at 70-80° C. Then, ARLACEL 165 VEG and POLYALDO 10-1-S were dissolved in the oil phase. Water and EUXYL PE 9010 were pre-mixed at 70-80° C. EUXYL PE 9010 is a liquid cosmetic preservative comprising phenoxyethanol and ethylhexylglycerin. The water phase premix was then added to the oil phase for emulsification of both phases. The mixture was cooled down to room temperature while mixing. COSMEDIA ATH was then added to the mixture with mixing.

TABLE 1

| | Example | | | | | | | |
|---|---|---|---|---|---|---|---|---|
| Trade Name | Comp A1 % wt | Comp A2 % wt | Comp A3 % wt | Comp A4 % wt | Ex A1 % wt | Ex A2 % wt | Ex A3 % wt | Ex A4 % wt |
| Water | 71 | 58.5 | 56 | 46 | 69 | 51 | 41 | 61 |
| Euxyl PE 9010 | 1 | 1 | 1 | 1 | 1 | 1 | 1 | 1 |
| UVAP | 10 | 15 | 20 | 20 | 10 | 10 | 20 | 10 |
| CETIOL CC | 15 | 22.5 | 20 | 30 | 15 | 30 | 30 | 15 |

TABLE 1-continued

| Trade Name | Comp A1 % wt | Comp A2 % wt | Comp A3 % wt | Comp A4 % wt | Ex A1 % wt | Ex A2 % wt | Ex A3 % wt | Ex A4 % wt |
|---|---|---|---|---|---|---|---|---|
| ARLACEL 165 VEG | 2 | 2 | 2 | 2 | 2 | 2 | 2 | 2 |
| NUVAP | | | | | 2 | 5 | 5 | 10 |
| COSMEDIA ATH | 1 | 1 | 1 | 1 | 1 | 1 | 1 | 1 |
| TOTAL | 100 | 100 | 100 | 100 | 100 | 100 | 100 | 100 |

Four of the eight compositions (Comp A1 through Comp A4) were comparative examples containing no added non UV-absorbing polyglycerol, whereas the other four of compositions were inventive examples formulated with added non UV-absorbing polyglycerol (POLYALDO 10-1-S) (Ex A1 through Ex A4). IN-VITRO SPF TEST testing for compositions listed in Table 1 was performed by loading the composition on PMMA plate with 1.3 mg/cm2 application density, shown in Table 2. The composition was spread to an even layer on the plate over the course of exactly one minute with constant pressure. IN-VITRO SPF TEST testing was performed in triplicate and mean and standard deviation are reported.

SPF boost was calculated as increase in the mean SPF of the particular composition as compared to a composition with the non UV-absorbing polyglycerol replaced with water. For example, the SPF Boost of Ex A1 is the SPF of Ex A1 minus the SPF of Comp A1 (Comp A1 is identical to Ex A1 except that Comp A1 had the non-UV-absorbing polyglycerol replaced with water. % SPF Boost was calculated as SPF boost divided by the SPF of the composition with the non-UV-absorbing polyglycerol replaced with water. For example, the % SPF Boost of Ex A1 is the SPF Boost of Ex A1 divided by the SPF of Comp A1. The results are shown in Table 2 and FIG. 1.

TABLE 2

| Example | % UVAP + % NUVAP | % UVAP | % NUVAP | % Oil | SPF (mean) | SPF (StDev) | SPF Boost | % SPF Boost |
|---|---|---|---|---|---|---|---|---|
| Comp A1 | 10 | 10 | 0 | 15 | 7.1 | 0.7 | 0.0 | |
| Comp A2 | 15 | 15 | 0 | 22.5 | 12.8 | 1.8 | 0.0 | |
| Comp A3 | 20 | 20 | 0 | 20 | 16.5 | 2.6 | 0.0 | |
| Comp A4 | 20 | 20 | 0 | 30 | 16.7 | 2.7 | 0.0 | |
| Ex A1 | 12 | 10 | 2 | 15 | 8.8 | 1.2 | 1.7 | 23.8 |
| Ex A2 | 15 | 10 | 5 | 30 | 22.1 | 3.7 | 15.0 | 210.0 |
| Ex A3 | 25 | 20 | 5 | 30 | 88.2 | 18.5 | 71.5 | 433.2 |
| Ex A4 | 20 | 10 | 10 | 15 | 10.5 | 1.1 | 3.4 | 47.5 |

Example 2

Varying weight percentages of UV-absorbing polyglycerol (UVAP) were mixed with a non UV-absorbing polyglycerol (NUVAP) and an oil to form sixteen different compositions. Six of the sixteen compositions (Comp B1 through Comp B6) were comparative examples containing no added non-UV-absorbing polyglycerol, whereas the other ten of compositions were inventive examples formulated with added non-UV-absorbing polyglycerol (POLYALDO 10-1-S) (Ex B1 through Ex B10). IN-VITRO SPF TEST testing for compositions listed in Table 3 was performed by applying each sample to PMMA plates with an application density of 1.3 mg/cm2. The sample was spread on the PMMA plate until a uniform layer was formed and the final mass of the coated plate was 26 mg. IN-VITRO SPF TEST testing was performed in triplicate and mean and standard deviation are reported.

SPF boost was calculated as increase in the mean SPF of the particular composition as compared to a composition with the non-UV-absorbing polyglycerol replaced with oil. For example, the SPF Boost of Ex B1 is the SPF of Ex B1 minus of SPF of Comp B1 (Comp B1 is identical to Ex B1 except that Comp B1 had non-UV-absorbing polyglycerol replaced with oil). % SPF Boost was calculated as SPF boost divided by the SPF of the composition with the non-UV-absorbing polyglycerol replaced with oil. For example, the % SPF Boost of Ex B1 is the SPF Boost of Ex B1 divided by the SPF of Comp B1. The results are shown in Table 3 and FIG. 1

TABLE 3

| Example | % UVAP + % NUVAP | % UVAP | % NUVAP | % Oil | SPF (mean) | SPF (StDev) | SPF Boost | % SPF Boost |
|---|---|---|---|---|---|---|---|---|
| Comp B1 | 10 | 10 | 0 | 90 | 13.6 | 1.6 | 0.0 | |
| Comp B2 | 20 | 20 | 0 | 80 | 21.5 | 2.6 | 0.0 | |
| Comp B3 | 30 | 30 | 0 | 70 | 26.8 | 4.0 | 0.0 | |
| Comp B4 | 40 | 40 | 0 | 60 | 25.6 | 4.5 | 0.0 | |
| Comp B5 | 50 | 50 | 0 | 50 | 21.8 | 4.6 | 0.0 | |
| Comp B6 | 60 | 60 | 0 | 40 | 22.8 | 4.9 | 0.0 | |
| Ex B1 | 12 | 10 | 2 | 88 | 14.0 | 2.4 | 0.4 | 3.0 |
| Ex B2 | 22 | 20 | 2 | 78 | 25.7 | 3.7 | 4.3 | 19.8 |
| Ex B3 | 32 | 30 | 2 | 68 | 38.4 | 5.3 | 11.6 | 43.4 |
| Ex B4 | 42 | 40 | 2 | 58 | 51.4 | 11.7 | 25.8 | 101.0 |
| Ex B5 | 52 | 50 | 2 | 48 | 62.3 | 9.8 | 40.5 | 185.4 |
| Ex B6 | 62 | 60 | 2 | 38 | 64.1 | 10.2 | 41.3 | 181.1 |
| Ex B7 | 20 | 10 | 10 | 80 | 23.8 | 5.3 | 10.2 | 75.3 |
| Ex B8 | 30 | 20 | 10 | 70 | 47.2 | 9.8 | 25.7 | 119.5 |
| Ex B9 | 25 | 10 | 15 | 75 | 28.4 | 5.7 | 14.8 | 108.8 |
| Ex B10 | 35 | 20 | 15 | 65 | 64.2 | 12.1 | 42.7 | 198.8 |

It can be seen from the tables that compositions of the present invention have substantially higher SPF values versus comparative compositions.

It is understood that while the invention has been described in conjunction with the detailed description thereof, that the foregoing description is intended to illustrate and not limit the scope of the invention.

The invention claimed is:

1. A sunscreen composition comprising:
a polymer composition comprising a linear UV-absorbing polyglycerol comprising a UV-absorbing chromophore covalently bound thereto; and
a cosmetically-acceptable topical carrier comprising at least one percent of a non-UV-absorbing polyglycerol, based on the total weight of said sunscreen composition.

2. The sunscreen composition of claim 1, wherein said cosmetically-acceptable topical carrier further comprises a hydrophobic diluent.

3. The sunscreen composition of claim 1, wherein said linear UV-absorbing polyglycerol is soluble in said hydrophobic diluent.

4. The sunscreen composition of claim 1, wherein the sum of the weight of said non-UV-absorbing polyglycerol and said linear UV-absorbing polyglycerol is at least twelve percent, based on the total weight of said sunscreen composition.

5. The sunscreen composition of claim 1, wherein said linear UV-absorbing polyglycerol comprises a hydrophobic moiety.

6. The sunscreen composition of claim 1, wherein said non-UV-absorbing polyglycerol comprises a hydrophobic moiety.

7. The sunscreen composition of claim 1, wherein said linear UV-absorbing polyglycerol comprises a hydrophobic moiety and said non-UV-absorbing polyglycerol comprises a hydrophobic moiety.

8. The sunscreen composition of claim 7, wherein said hydrophobic moiety has an average number of carbon atoms that is from 8 to 30.

9. The sunscreen composition of claim 1, wherein said linear UV-absorbing polyglycerol comprises a first hydrophobic moiety having a first average number of carbon atoms and said non-UV-absorbing polyglycerol comprises a second hydrophobic moiety having a second average number of carbon atoms, wherein said first average number of carbon atoms and said second average number of carbon atoms are within 10 carbon atoms of one another.

10. The sunscreen composition of claim 1, wherein said linear UV-absorbing polyglycerol has a first average degree of glycerol polymerization and said non-UV-absorbing polyglycerol has a second average degree of glycerol polymerization, and wherein said first average degree of glycerol polymerization and said second average degree of glycerol polymerization are each from about 2 to about 20.

11. The sunscreen composition of claim 1, comprising about two percent or more of said non-UV-absorbing polyglycerol and about ten percent or more of said linear UV-absorbing polyglycerol.

12. The sunscreen composition of claim 1 wherein said UV-absorbing chromophore is selected from the group consisting of a transesterification product of 3-(3-(2H-benzo[d][1,2,3]triazol-2-yl)-5-(tert-butyl)-4-hydroxyphenyl) propanoic acid with polyethylene glycol 300, benzenepropanoic acid, 3-(2H-benzotriazol-2-yl)-5-(1, 1-dimethylethyl)-4-hydroxy-, C7-9-branched and linear alkyl esters, 6-octyl-2-(4-(4,6-di([1,1'-biphenyl]-4-yl)-1,3,5-triazin-2-yl)-3-hydroxyphenoxy) propanoate, 3-(3-(2H-benzo[d][1,2,3]triazol-2-yl)-5-(tert-butyl)-4-hydroxyphenyl) propanoic acid, and polyethylene glycol ester of 3-[3-(2H-1,2,3-benzotriazol-2-yl)-5-tert-butyl-4-hydroxyphenyl]propanoate.

13. The sunscreen composition of claim 1 wherein said UV-absorbing chromophore is 3-(3-(2H-benzo[d][1,2,3]triazol-2-yl)-5-(tert-butyl)-4-hydroxyphenyl) propanoic acid.

14. The sunscreen composition of claim 1 comprising from about 5 percent to about 50 percent by weight of said linear UV-absorbing polyglycerol.

15. The sunscreen composition of claim 1 comprising about 10 percent or more of said linear UV-absorbing polyglycerol.

16. The sunscreen composition of claim 1 wherein said sunscreen composition is essentially free of non-polymeric UV-absorbing sunscreen agents.

17. The sunscreen composition of claim 1 wherein said sunscreen composition is essentially free of a sunscreen agent other than said UV-absorbing polyglycerol.

18. The sunscreen composition of claim 1 comprising a sunscreen agent selected from the group consisting of a UV-absorbing polymer other than said linear UV-absorbing polyglycerol, a non-polymeric UV-absorbing sunscreen agent and non-UV-absorbing, light-scattering particles.

19. A sunscreen composition comprising:
a polymer composition comprising a linear UV-absorbing polyglycerol comprising a UV-absorbing chromophore covalently bound thereto; and
a cosmetically-acceptable topical carrier comprising at least one percent of a non-UV-absorbing polyglycerol, based on the total weight of said sunscreen composition, wherein said UV-absorbing chromophore is polyethylene glycol ester of 3-[3-(2H-1,2,3-benzotriazol-2-yl)-5-tert-butyl-4-hydroxyphenyl] propanoate.

* * * * *